(12) United States Patent
Wong

(10) Patent No.: US 7,919,238 B2
(45) Date of Patent: Apr. 5, 2011

(54) METHOD FOR RAPID IDENTIFICATION OF ALTERNATIVE SPLICING

(75) Inventor: Albert J. Wong, Menlo Park, CA (US)

(73) Assignee: Albert J. Wong, Menlo Park, CA (US)

( * ) Notice: Subject to any disclaimer, the term of this patent is extended or adjusted under 35 U.S.C. 154(b) by 826 days.

(21) Appl. No.: 10/567,808

(22) PCT Filed: Jul. 26, 2004

(86) PCT No.: PCT/US2004/023848
§ 371 (c)(1),
(2), (4) Date: Jun. 18, 2007

(87) PCT Pub. No.: WO2005/017186
PCT Pub. Date: Feb. 24, 2005

(65) Prior Publication Data
US 2008/0153086 A1   Jun. 26, 2008

Related U.S. Application Data

(60) Provisional application No. 60/493,759, filed on Aug. 8, 2003.

(51) Int. Cl.
*C12Q 1/68* (2006.01)

(52) U.S. Cl. .......................................................... 435/6

(58) Field of Classification Search .................. None
See application file for complete search history.

(56) References Cited

U.S. PATENT DOCUMENTS

| | | | |
|---|---|---|---|
| 5,552,278 A | 9/1996 | Brenner | 435/6 |
| 5,589,339 A | 12/1996 | Hampson et al. | 435/6 |
| 5,643,729 A | 7/1997 | Taniguchi et al. | 435/6 |
| 5,876,932 A | 3/1999 | Fischer | 435/6 |
| 5,986,076 A | 11/1999 | Rothschild et al. | 536/22.1 |
| 6,110,684 A | 8/2000 | Kemper et al. | 435/6 |
| 6,232,073 B1 | 5/2001 | Ware et al. | 435/6 |
| 6,251,590 B1 * | 6/2001 | Schweighoffer et al. | 435/6 |
| 6,291,170 B1 | 9/2001 | Van Gelder et al. | 435/6 |
| 6,372,432 B1 | 4/2002 | Tocque et al. | 435/6 |
| 6,475,736 B1 | 11/2002 | Stanton, Jr. | 435/6 |
| 6,500,650 B1 | 12/2002 | Stanton, Jr. et al. | 435/91.1 |
| 6,632,610 B2 | 10/2003 | Thill | 435/6 |
| 2004/0110191 A1 * | 6/2004 | Winkler et al. | 435/6 |

FOREIGN PATENT DOCUMENTS

| | | |
|---|---|---|
| WO | WO 02/31190 | 4/2002 |
| WO | WO 02/061143 | 8/2002 |
| WO | WO 2004/053163 | 6/2004 |

OTHER PUBLICATIONS

Huerta et al., "Alternative mRNA splicing in colon cancer causes loss of expression of neural cell adhesion molecule", *Surgery* 130(5): 834-843, 2001.

Yang et al., "Combining SSH and cDNA microarrays for rapid identification of differentially expressed genes", *Nucleic Acids Research* 27(6): 1517-1523, 1999.

Carninci et al., "High-Efficiency Full-Length cDNA Cloning", *Methods in Enzymology* 303: 19-44, 1999.

Mary et al., "A tumor specific single chain antibody dependent gene expression system", *Oncogene* 18: 559-564, 1999.

* cited by examiner

*Primary Examiner* — Gary Benzion
*Assistant Examiner* — Cynthia B Wilder
(74) *Attorney, Agent, or Firm* — Pepper Hamilton LLP

(57) ABSTRACT

Alternatively spliced RNA, along with their normally-spliced counterparts, can be rapidly identified by hybridizing cDNA from normal tissue to cDNA from an abnormal or test tissue. The two cDNA populations are separately tagged prior to hybridization, which allows isolation of double-stranded cDNA containing both normal and alternatively spliced molecules. Within this population, pairing of cDNA molecules representing an alternatively spliced mRNA with cDNA molecules representing the counterpart normally spliced mRNA will form double-stranded cDNA with single-stranded mismatched regions. The mismatched double-stranded cDNA are isolated with reagents that bind single-stranded nucleic acids. The strands of each mismatched double-stranded cDNA are then coupled and analyzed, simultaneously identifying both normal and alternatively spliced molecules.

40 Claims, 7 Drawing Sheets

SEQUENCE LISTING

<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: chemically synthesized selectable tag

<400> SEQUENCE: 1
gtcatgcata gcaattgtcg ac                                             22

<210> SEQ ID NO 2
<211> LENGTH: 17
<212> TYPE: DNA
<213> ORGANISM: Artificial Sequence
<220> FEATURE:
<223> OTHER INFORMATION: chemically synthesized selectable tag

<400> SEQUENCE: 2
tcccccgggg ggaatcg                                                   17

<210> SEQ ID NO 3
<211> LENGTH: 27
<212> TYPE: DNA
<213> ORGANISM: Artificial Sequence
<220> FEATURE:
<223> OTHER INFORMATION: chemically synthesized selectable tag

<400> SEQUENCE: 3
atgcatagca acctcacgtg tgaatcg                                        27

<210> SEQ ID NO 4
<211> LENGTH: 21
<212> TYPE: DNA
<213> ORGANISM: Artificial Sequence
<220> FEATURE:
<223> OTHER INFORMATION: chemically synthesized affinity medium

<400> SEQUENCE: 4
acacgtgagg ttgctatgca t                                              21

<210> SEQ ID NO 5
<211> LENGTH: 58
<212> TYPE: DNA
<213> ORGANISM: Artificial Sequence
<220> FEATURE:
<223> OTHER INFORMATION: chemically synthesized polynucleotide linking
     moiets

<400> SEQUENCE: 5
acacgatccg cagatgtccg cagttattcc tttttttggaa taactgcgga catctgcg     58

<210> SEQ ID NO 6
<211> LENGTH: 30
<212> TYPE: DNA
<213> ORGANISM: Artificial Sequence
<220> FEATURE:
<223> OTHER INFORMATION: chemically synthesized arbitrary sequence

<400> SEQUENCE: 6
aaattcctat gcatgctcaa tggactgtgt                                     30

METHOD FOR RAPID IDENTIFICATION OF ALTERNATIVE SPLICING

FIELD OF THE INVENTION

The present invention relates to a method for isolating and identifying alternatively spliced mRNA.

BACKGROUND OF THE INVENTION

The number of proteins produced by the human genome likely numbers in the hundreds of thousands. However, recent evidence indicates that the human genome contains only 30,000 to 45,000 different genes. Clearly, each gene is producing multiple proteins.

Alternative splicing of primary RNA transcripts is a major mechanism for increasing production of proteins from the human genome. It is known that 30% to 60% of genes undergo alternative splicing to produce messenger RNA (mRNA). Modrek B et al. *Nat. Genet.* 30, 13-19 (2002). These alternatively spliced mRNA are translated into alternative splice form proteins that contain amino acid sequences different than the corresponding protein produced by normally spliced mRNA.

Alternative splice form proteins are often expressed in a tissue-specific manner, or under certain physiologic or disease states. Modrek B et al., *Nucl. Acids Res.* 29, 2850-2859 (2001). Consequently, certain alternatively spliced mRNA are present in a limited number of cells in a subject suffering from a given disease or condition. For example, it is known that many types of cancer cells produce alternative splice forms which are not found in normal cells from the same subject. Cancer-associated genes such as CD44 (Rodriguez C et al., *Int. J. Cancer* 64, 347-354, 1995), estrogen receptor (Castles C G et al., *Cancer Res.* 53, 5934-5939, 1993), FGF receptor (Luqmani Y A et al., *Int. J. Cancer* 64, 274-279, 1995), DNA polymerase (Bhattacharyya N et al., *DNA Cell Biol.* 18, 549-554, 1999), cathepsin B (Gong Q et al., *DNA Cell Biol.* 12, 299-309, 1993), FHIT (Panagopoulos I. et al., *Cancer Res.* 56, 4871-4875, 1996), BRCA1 (Thakur S et al., *Mol. Cell Biol.* 17, 444-452, 1997) and BRCA2 (Bieche I et al., *Cancer Res.* 59, 2546-2550, 1999), produce alternatively spliced mRNA that are specifically expressed in cancerous tissues. Other disease states in which alternative splice forms are specifically produced in certain tissues include diabetes, Alzhiemer's disease and systemic lupus erythematosus (SLE).

Drugs that target proteins specific to cancerous or other disease tissue have proven efficacious in the appropriate patient population. For example, successful treatment of breast cancer has been reported for drugs which target the estrogen receptor (Jordan C, *Clin. Ther.* 24 Suppl A, A3-16, 2002) or the HER-2 receptor (Thomssen C, *Anticancer Drugs* 12 Suppl 4, S19-S25, 2001; Yip Y L et al., *Cancer Immunol. Immunother.* 50; 569-587, 2002). The genetic alterations present in tumor-specific proteins, such as mutations in p53, BRCA 1 and BRCA2, provide another source of targets. Thus, the proteins produced from alternatively spliced mRNA produced specifically in cancers or other disease states are also attractive therapeutic targets.

However, proteins produced from alternatively spliced mRNA have not been widely exploited as therapeutic targets. The major impediment to using such proteins as therapeutic targets has been the incidental or tedious nature by which alternatively spliced mRNA are found. Present methodologies are limited to either cDNA cloning (which is highly labor intensive) or RT/PCR (which focuses only on known portions of genes). In addition, most cloning- and RT/PCR-based methods are highly biased, as they require prior knowledge of the alternatively spliced mRNA sequence.

An unbiased procedure for discovery of alternatively spliced mRNA has been reported in U.S. Pat. No. 6,251,590 of Schweighoffer et al. However, the Schweighoffer et al. method identifies only the region in the alternatively spliced mRNA that is different from the normally spliced mRNA. The cDNA corresponding to both the normal and alternatively spliced mRNA must be separately cloned in order to pinpoint the alternatively spliced region in the context of the full-length molecule. The sequencing of multiple cDNA clones is also required to determine the prevalence of a given alternatively spliced mRNA. The Schweighoffer et al. method thus required a substantial investment of both time and resources in order to identify alternatively spliced molecules.

Thus, an unbiased method of rapidly and easily identifying alternatively spliced RNA in biological sample is needed, in which both the full-length normal and alternatively spliced mRNA are simultaneously isolated for comparison. Ideally, such a method would not rely on multiple cloning and sequencing steps for determining the identity and relative abundance of alternative splice forms in a given sample.

SUMMARY OF THE INVENTION

The present invention is directed to an unbiased method for isolating and identifying full-length alternatively spliced RNA, wherein the alternatively spliced RNA is isolated in conjunction with its counterpart normally spliced RNA. The practice of this method thus does not require foreknowledge of either the normal or alternatively spliced RNA sequences, or the nature of the alternative splice. The method also does not require multiple cloning or sequencing steps in order to identify the alternatively spliced RNA.

The invention provides a method of identifying an alternatively spliced RNA by comparing populations of cDNA molecules obtained from two biological samples. One sample represents a first physiological condition, and the other sample represents a second physiological condition. The two cDNA populations are separately tagged with different compounds, and denatured portions of each tagged cDNA population are annealed to each other under conditions which allow the formation of a mixed population of cDNA molecules. This mixed population comprises single-stranded cDNA molecules from both populations, double-stranded cDNA comprising cDNA molecules from only the first or second cDNA populations, and double-stranded cDNA comprising cDNA molecules from both the first and second cDNA populations.

Double-stranded cDNA comprising cDNA molecules from both the first and second cDNA populations are isolated from the mixed population by first selecting for those molecules comprising the tag specific to the first cDNA population, followed by selecting for molecules which also contain the tag specific to the second cDNA population. Alternatively, double-stranded cDNA comprising cDNA molecules from both the first and second cDNA populations can be isolated by selecting for molecules comprising the tag specific to the second cDNA population, followed by selecting for molecules comprising the tag specific to the first cDNA population.

The double-stranded cDNA selected above comprises two types. The first type comprises two cDNA molecules with perfectly matched sequences, in which each cDNA molecule represents normally spliced mRNA. The second type comprises two cDNA molecules with at least one area of mismatched sequence. In the second type of double-stranded cDNA, one cDNA strand represents the alternatively spliced mRNA molecule and the other cDNA strand represents the normally spliced counterpart of the alternatively spliced mRNA.

The mismatched sequence is unpaired with respect to the opposite strand and comprises a single-stranded region in the otherwise paired sequences. Such a double-stranded cDNA encompassing a mismatched sequence is then isolated with reagents which bind to regions of single-stranded nucleic acid. The two nucleic acid strands of said selected double-stranded cDNA are coupled, yielding a single molecule that can be analyzed to identify the normal and alternatively spliced molecules.

A kit comprising some or all of the components and for performing the present method, along with instructions for their use, is also provided.

DETAILED DESCRIPTION OF THE INVENTION

The present method can be used to isolate and identify RNA molecules which are alternatively spliced in the cells of a first biological sample, as compared to RNA produced in the cells of a second biological sample. The alternatively spliced RNA molecule is simultaneously isolated with its normally spliced counterpart RNA molecule.

As used herein, an "alternatively spliced RNA" is an RNA molecule transcribed from a gene in cells of one biological sample, which is spliced differently from an RNA molecule transcribed from the same gene in cells of a reference biological sample. The RNA molecule transcribed from the same gene in cells of the reference biological sample is the "normally spliced counterpart RNA molecule" of the alternatively spliced RNA. A biological sample typically contains a plurality of different alternatively spliced RNA molecules. Thus, the present method can simultaneously isolate and identify a plurality of alternatively spliced RNA molecules in conjunction with their normally spliced counterparts.

Figure 1:
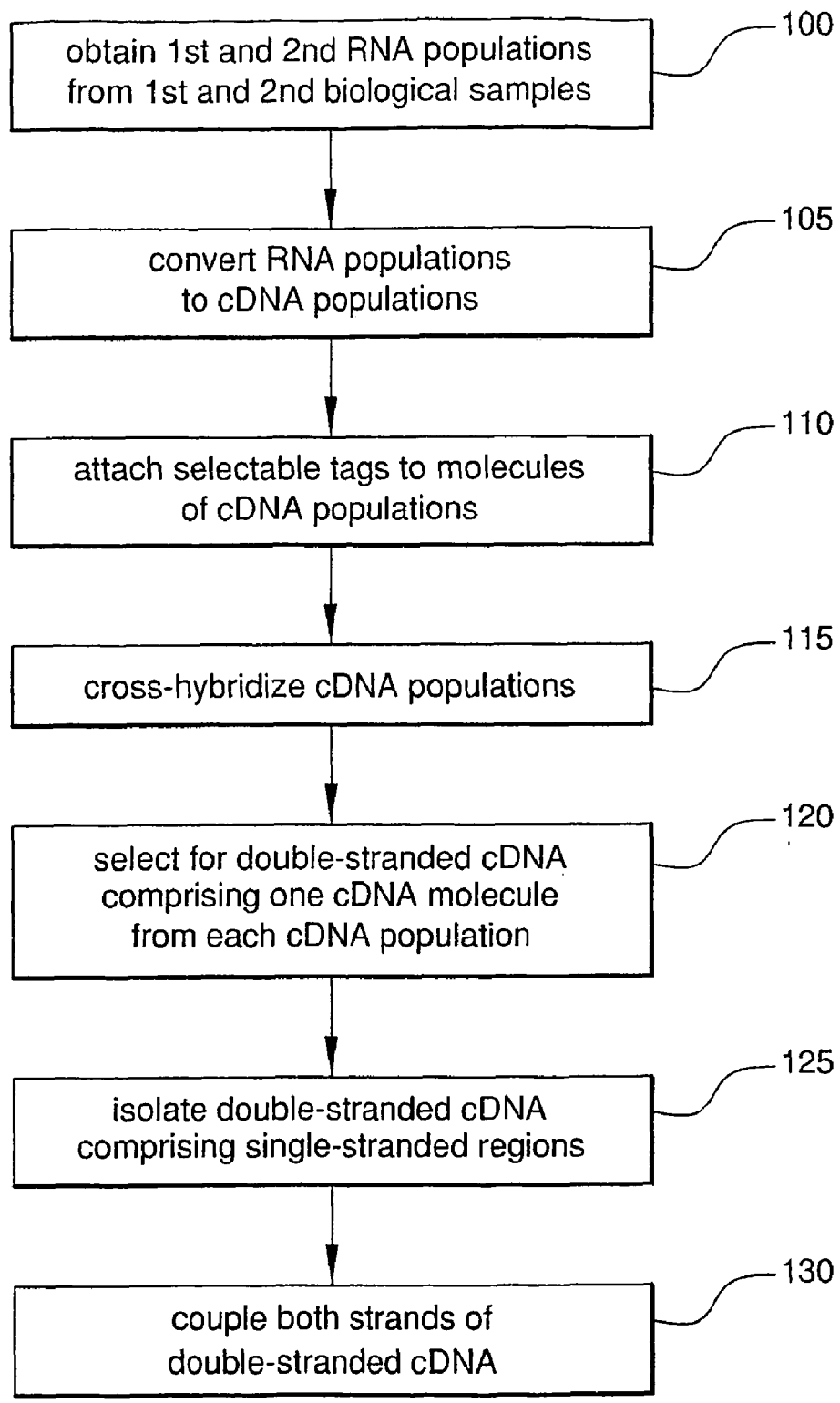
FIG. 1 is a flow chart of a method according to the invention.

A flow chart of the present method is provided in FIG. 1. With reference to the figure, first and second RNA populations comprising alternatively spliced RNA are obtained from first and second biological samples, respectively (step 100). The RNA populations are then converted to cDNA for subsequent manipulations (step 105). As the practice of the present method involves hybridization of complementary cDNA molecules from each cDNA population, preferably at least one, and more preferably both, cDNA populations comprise double-stranded cDNA. In step 110, selectable tags are attached to the molecules of the first and second cDNA populations. The selectable tags used for each population are different.

Substantially all of the cDNA molecules from each tagged cDNA population are denatured and annealed, so that single-stranded cDNA molecules from one cDNA population hybridize with complementary single-stranded cDNA molecules from the other cDNA population (step 115). This step is also known as "cross-hybridization." The double-stranded cDNA molecules which comprise one strand from each cDNA population also comprise both selectable tags. These molecules can therefore be isolated by selection for one tag, followed by selection for the other tag (step 120).

The two strands of each double-stranded cDNA selected in step 120 have perfectly matched sequences, or have a mismatched sequence which represents an alternatively spliced region in one of the strands. The mismatched sequences manifest as single-stranded regions within the cDNA duplex. Double-stranded cDNA with mismatched sequences are therefore isolated by reagents which selectively bind single-stranded DNA (step 125). The strands of each cDNA duplex isolated in step 125 represent linked pairs of normal and alternatively spliced molecules. The two strands of each duplex isolated in step 125 are thus coupled together, so that the relationship of each pair of normal and alternatively spliced molecules is fixed (step 130). The coupled molecules produced in step 130 represent different pairs of alternatively spliced and normal molecules. Each coupled molecule can be expanded through cloning or the polymerase chain reaction. These coupled molecules can then be analyzed to obtain information about the molecules; e.g., sequence data, relative abundance, and the like.

Any type of biological material comprising nucleic acids can be used as the first and second biological samples. For example, first and second biological samples can be derived from prokaryotes; lower eukaryotes (e.g., yeasts, fungi and the like); and higher eukaryotes such as birds, fish, reptiles, and mammals. Preferably, the biological samples are derived from mammals, especially canines, felines, rodents (e.g., mice and rats), bovines, ovines, porcines and primates (e.g., humans). In a particularly preferred embodiment, the biological samples are derived from humans. As used herein, "derived from" with respect to a biological sample includes tissue or cells obtained directly from a subject (e.g., blood or biopsy material), or cells or tissue which have been maintained ex vivo for any length of time, such as cell, tissue and organ cultures.

The first and second biological samples can represent any two physiological or genetic states. For example, the first and second biological samples can comprise diseased and normal tissue, tissue in different developmental states, or tissue which has been treated with a therapeutic or toxic agent as compared with untreated tissue. The first and second biological samples can also comprise tissue or cells from different, but preferably related, species. The presence of alternatively spliced RNA in a particular biological sample as compared to another can thus be used as a marker of a given physiological condition, or can be used to develop therapeutic agents which target only the cells producing the alternatively spliced RNA.

Generally, the first and second biological samples are derived from the same subject or from subjects of the same species, and represent alternative physiological states. Preferably, the first and second biological samples comprise cells from normal and diseased tissue, respectively. Diseased cells or tissue can be obtained, for example, from a subject with: infections or stress; cancers or neoplasias (e.g., acute promyelocytic leukemia; acute lymphoblastic leukemia; myeloblastic leukemia; uterine cancer; thyroid cancer; gastrointestinal tumors; dysplastic and neoplastic cervical epithelium; melanoma; breast cancer; prostate cancer; lung cancer; endometrial cancer; teratocarcinoma; colon cancer; brain or desmoplastic round cell tumors; epithelial neoplasias; gastric cancer; ovarian cancer; sarcomas, myomas, myxomas, ependymomas, fibromas, and neurofibrosarcomas); disorders or conditions of the imniune system (e.g., allergic response, x-linked agammaglobulinemia, immunity/inflammation, systemic lupus erythematosus, Goodpasture disease); metabolic disorders (e.g., phenylketonuria, non-insulin dependent diabetes); collagen disorders (e.g., osteogenesis imperfecta); psychiatric disorders; skin disorders, liver disorders; disorders of the arteries (atherosclerosis); inherited red cell membrane disorders (e.g., hereditary elliptocytosis); thyroid hormone repression; endometrial hyperplasia; Alzheimer's disease; and alcoholism. In a particularly preferred embodiment, the first and second biological samples comprise cells from normal and tumor or neoplastic tissue, respectively.

Diseased cells or tissues can be readily identified by certain phenotypic abnormalities which are apparent to by those skilled in the art upon examination of the cells or tissue. See, for example, the pathology and histopathology of different cancers is described in *Cancer: Principles and Practice of Oncology*, (3rd edit., DeVita V T, Hellman S, and Rosenberg S A, eds.), 1989, J. B. Lipincott Co., Phila., PA.

Cells which are tumorigenic or neoplastic can also be identified by certain growth characteristics and morphology exhibited by the cell in culture. Tumorigenic or neoplastic cells are insensitive to contact-induced growth inhibition, and the cells form foci in the culture vessel when cultured for extended periods. Tumorigenic or neoplastic cells also exhibit characteristic morphological changes, disorganized patterns of colony growth, and the acquisition of anchorage-independent growth.

Tumorigenic or neoplastic cells also have the ability to form invasive tumors in susceptible animals, which can be assessed by injecting the cells, for example, into athymic mice or newborn animals of the same species using techniques well-known in the art. See, for example, Combes et al. (1999), "*Cell Transformation Assays as Predictors of Human Carcinogenicity: The Report and Recommendations of ECVAM Workshop 39*," *ATLA* 27, 745-767. Other histological and cell culture-based techniques for identifying diseased cells are also within the skill in the art.

In the practice of the invention, RNA populations are separately isolated from a first and a second biological sample. As used herein, a "population of RNA molecules" or "RNA population" refers to a group of individual RNA molecules which are representative of the RNA produced by cells in a biological sample, from which some or all of the RNA molecules are taken for further processing according to the present method.

RNA populations for use in the present method can be obtained from a biological sample by techniques which are familiar to those skilled in the art. Such techniques generally comprise lysis of cells or tissues and recovery of RNA by means of extraction procedures. In particular, RNA populations can be obtained by treatment of biological samples with chaotropic agents such as guanidinium thiocyanate, followed by RNA extraction with solvents (e.g., phenol and chloroform). See, e.g., Sambrook J et al., *Molecular Cloning: A Laboratory Manual*; Second Edition, Cold Spring Harbor Laboratory, Cold Spring Harbor, N.Y., 1989. and Chomczynski et al., *Anal. Biochem.*, 162, 156-159, 1987. Preferably, RNA populations for use in the present method are enriched for polyA+ RNA by standard techniques, such as purification with oligo(dT) cellulose. As used herein, "polyA+ RNA" refers to RNA which comprises a homopolymer of adenosine monophosphate residues (typically from 20-200 nucleotides in length) on the 3' end. Generally, polyA+ RNA comprises eukaryotic messenger RNA.

Techniques for obtaining RNA populations from a biological sample can be readily implemented with commercially available kits, such as the RNeasy™ kit available from Qiagen, Inc. (Valencia, Calif.), the RiboPure™ kit available from Ambion (Austin, Tex.) and Eppendorf Phase Lock Gel available from Brinkmann Instruments, Inc. (Westbury, N.Y.). Techniques for obtaining RNA populations enriched for polyA+ RNA can be also readily implemented with commercially available kits, such the Poly(A)Pure™ kit available from Ambion (Austin, Tex.) or the polyA Spin™ mRNA isolation kit available from New England Biolabs, Inc. (Beverly, Mass.). RNA populations suitable for use in the present method can also be obtained directly from libraries or samples which have been prepared beforehand and stored under suitable conditions. It is understood that the RNA molecules comprising the RNA populations for use in the present method need not be in a fully pure state. For example, traces of genomic DNA, proteins or other cellular components (in as much as they do not significantly affect RNA stability) will not significantly affect the practice of the present method.

RNA populations obtained from biological samples can be used immediately, or can be stored for later use. Suitable storage conditions for RNA are familiar to those skilled in the art, and include storage in the cold, preferably at −70° C. in an aqueous, RNase-free solution or in the RNA extraction buffer at temperatures from −20° C. to −70° C.

The amount of RNA in RNA population can vary depending on the sample type and the extraction method used. Generally, total RNA populations for use in the present method comprises from about 0.1 microgram of to about 10 micrograms of RNA, preferably about 5 micrograms of RNA. Suitable polyA+ RNA-enriched populations for use in the present method generally comprise at least about 0.05 microgram of RNA to about 2 micrograms RNA, preferably about 1 microgram of RNA. RNA population comprising sufficient quantities of RNA molecules for use in the present method can be obtained from biological samples comprising from about $10^5$ to about $10^8$ cells, or biological samples comprising about 0.5 gram to about 5 grams of tissue.

Because RNA is generally unstable once removed from the cellular environment, the present method is performed with RNA populations in which the RNA molecules, preferably only the polyA+ RNA molecules, have been converted into "complementary DNA" or "cDNA" by reverse-transcription. Conversion of the RNA molecules in an RNA population to cDNA creates a corresponding population of cDNA molecules. As used herein, a "population of cDNA molecules" or "cDNA population" refers to a group of individual cDNA molecules corresponding to individual RNA molecules from an RNA population, from which some or all of the cDNA molecules are taken for further processing according to the present method.

Generally, cDNA populations for use in the present method are obtained by producing "first-strand" cDNA from the RNA molecules of an RNA or polyA+ RNA-enriched population. Each first-strand cDNA molecule is complementary to the RNA molecule from which is was reverse-transcribed. First-strand cDNA synthesis can be accomplished using an RNA-dependent DNA polymerase enzyme (also called a "reverse transcriptase") and a suitable oligonucleotide primer, using standard techniques within the skill in the art; see, e.g., Sambrook et al., supra; Kotewicz et al., *Gene* 35, 249, 1985; Krug M M et al., *Meth. Enzymol.* 152, 316, 1987 and Gubler U et al., *Gene* 25, 263-269, 1983. Suitable primers for reverse-transcription of RNA include single-stranded DNA hexamers comprising random sequences and polydeoxythymidylic acid or "oligo(dT)." A preferred primer comprises oligo(dT)

from about 12 to about 18 nucleotides in length, as such primers will reverse transcribe only the polyA+ RNA in an RNA population.

Reverse transcriptases suitable for use in the present method are generally known in the art, and include those derived from Avian Myeloblastosis Virus (AMV) and from Moloney Murine Leukemia Virus (MMLV). AMV and MMLV reverse transcriptases and kits for generation of "first-strand" cDNA are commercially available, for example, from Invitrogen, Inc. (Carlsbad, Calif.), New England Biolabs, Inc. (Beverly, Mass.) and Promega Corp. (Madison, Wis.). Certain thermostable DNA polymerases, such as those isolated from *Thermus flavus* and *Thermus thermophilus* HB-8, also have reverse transcriptase activity. *T. flavus* and *T. thermophilus* HB-8 DNA polymerases are commercially available from Promega Corp. (Madison, Wis.).

Preferred reverse-transcriptases are those which possess, or have been modified to possess, the ability to reverse transcribe RNA molecules over 3 kb in length. For example, MMLV reverse transcriptases which has been modified to remove the intrinsic RNase H activity allow the synthesis of cDNA up to 12 kb in length, with high fidelity to the original RNA sequence. Examples of such modified MMLV reverse transcriptases include the BioScript™ reverse transcriptase from Bioline USA, Inc. (Randolph, Mass.) and the SuperScript™ II RT from Invitrogen Life Technologies (Carlsbad, Calif.).

First-strand cDNA can be used in the present method without further processing, or can be subjected to a second round of DNA synthesis to produce a "second-strand" cDNA. Each molecule of second-strand cDNA is complementary to the first-strand cDNA molecule from which is was synthesized. Under conditions which promote annealing of nucleic acids, complementary first- and second-strand cDNA molecules exist as a DNA duplex, which is hereinafter referred to as "double-stranded cDNA." In the practice of the present method, the first strand cDNA molecules of at least one of the cDNA populations are converted into double-stranded cDNA.

Techniques for synthesizing second-strand cDNA from first-strand cDNA are also within the skill in the art; see, e.g., Sambrook et al., 1989, supra and Gubler U et al., *Gene* 25, 263-269, 1983. In one such technique, the RNA template is removed from the first-strand cDNA with NaOH or RNase H. The 3' end of the first-strand cDNA then forms a hairpin-like structure that primes synthesis of the second-strand cDNA by a DNA-dependent DNA polymerase. Suitable DNA-dependent DNA polymerases include *E. coli* DNA polymerase I (or the Klenow fragment); T4 DNA polymerase; and reverse transcriptases with DNA-dependent DNA polymerase activity such as AMV and MMLV reverse transcriptases.

Another technique for synthesizing second-strand cDNA involves the "replacement synthesis" of second-strand cDNA. In this technique, an enzyme such as RNase H produces nicks and gaps in the RNA strand of the cDNA:RNA hybrid produced during first-strand cDNA synthesis. The nicked and gapped RNA strand is used as a series of primers by a DNA-dependent DNA polymerase for synthesis of the second-strand of cDNA.

Double-stranded cDNA synthesized as described above can contain hairpin turns and single-stranded overhangs. In the practice of the present method, the double-stranded cDNA are preferably blunt-ended using standard enzymes and techniques familiar to those skilled in the art. For example, hairpin turns can be removed from double-stranded cDNA by treatment with nuclease S1 under standard conditions. Single-stranded overhangs on double-stranded cDNA molecules can be removed with enzymes which either degrade or fill in the single-stranded overhangs, or by restriction endonucleases which create blunt ends on digestion of double-stranded DNA.

Examples of enzymes which degrade single-stranded overhangs on double-stranded DNA include mung bean nuclease; nuclease S1; Klenow fragment (degrades 3' overhangs); and T4 DNA polymerase (degrades 3' overhangs). Examples of enzymes which fill-in single-stranded overhangs on double-stranded DNA include Pfu polymerase; Klenow fragment in the presence of nucleotides (fills in 5' overhangs); and T4 DNA polymerase (fills in 5' overhangs).

Examples of restriction endonucleases which create blunt ends on digestion of double-stranded DNA include Afe I; Alu I; BmgB I; BsaA I; BsrB I; BstU I; BstZ17 I; Dra I; Eco RV; Fsp I; Hae III; Hpa I; Hinc II; Msc I; Msp Al I; Nae I, Nru I; Pme I; Pml I; Pvu II; Rsa I; Sca I; Sfo I; Sma I; SnaB I; Ssp I; Stu I; and Swa I. A preferred restriction endonuclease is Eco RV. In a particularly preferred embodiment, double-stranded cDNA molecules are digested with a restriction endonuclease to create blunt-ends comprising a naturally occurring nucleotide sequence.

The cDNA populations for use in the present method can be used immediately, or can be stored for later use. Suitable storage conditions for cDNA are familiar to those skilled in the art, and include storage in the cold, preferably at −20° C. in an aqueous, DNase-free solution.

After synthesis of cDNA populations as described above, a selectable tag is attached to the cDNA molecules of each cDNA population. The tag attached to the cDNA molecules of the first cDNA population is different from the tag attached to the cDNA molecules of the second cDNA population. The selectable tags can comprise any compound which allows differential separation of the cDNA molecules after cross-hybridization of molecules from the first and second cDNA populations. As is described in more detail below, these tags are used in subsequent steps to isolate double-stranded cDNA which comprise one cDNA molecule from the first cDNA population and one cDNA molecule from the second cDNA population.

Generally, selectable tags useful in the present invention comprise one compound of an affinity pair. As used herein, an "affinity pair" refers to two compounds or structures with a specific affinity for each other. Suitable affinity pairs include biotin and avidin/streptavidin; antigens or haptens and their corresponding antibodies; hormones, vitamins, metabolites or pharmacological agents and their corresponding receptors; carbohydrates and lectins; metals and chelators; complementary polynucleotide sequences (including homopoly-nucleotides such as poly dG:poly dC, poly dA:poly dT, and poly dA:poly U); cofactor or prosthetic groups and apoproteins; effector molecules and their receptors; hydrophobic interactive pairs; enzyme cofactors and enzymes; polymeric acids and bases; dyes and protein binders; peptides and specific protein binders (e.g., ribonuclease, S-peptide and ribonuclease S protein); and enzyme inhibitors (reversible and irreversible) and enzymes.

In one embodiment, the selectable tag comprises a lectin. Suitable lectins include C-type or Ca2+-dependent lectins, Gal-binding galectins, P-type Man 6-phosphate receptors, I-type lectins including sialoadhesins and other immunoglobulin-like sugar-binding lectins, and L-type lectins related in sequence to the leguminous plant lectins (see, e.g., Drickamer K, *Curr. Opin. Struct. Biol.* 5, 612-616, 1995; Drickamer et al., *Annu. Rev. Cell Biol.* 9, 237-264, 1993; and Powell L D et al., *J. Biol. Chem.* 270, 14243-14246, 1995). Preferably, the selectable tag comprises a biotin or avidin/streptavidin molecule, or a polynucleotide sequence.

Techniques for attaching tags to cDNA molecules are within the skill in the art. For example, biotins can be attached to cDNA molecules by incorporating a nucleotide comprising the biotin molecule (e.g., biotin-11-dUTP) during first- or second-strand synthesis, according to standard techniques. Alternatively, biotin can be attached to cDNA molecules by a spacer arm, for example with one or more ε-aminocaproic acid moieties. Polynucleotide tags can be attached to the cDNA molecules by standard molecular biology techniques, for example by blunt-end ligation. See, e.g., Sambrook et al., 1989, supra.

Preferably, selectable tags are releasable or comprise a portion which can be cleaved, for example by chemical, enzymatic or physical means. Physical cleavage includes cleavage by application of light or other electromagnetic radiation. Exposure of cDNA comprising a cleavable or releasable selectable tag to the appropriate conditions will cause separation of the tag (or a portion thereof) from the cDNA.

For example, polynucleotide or polypeptide tags can comprise a specific chemical or enzymatic cleavage site, as are known in the art. Chemically cleavable and photocleavable biotins are also known, for example as described in U.S. Pat. No. 5,986,076, the entire disclosure of which is herein incorporated by reference. Examples of chemically cleavable biotins include NHS—SS-biotin, which can be linked to another molecule through a disulfide bond and an N-hydroxysuccinimide ester group that reacts selectively with primary amines. The biotin portion of NHS—SS-biotin can be removed by cleaving the disulfide bond with thiols. NHS—SS-biotin is commercially available as Immunopure NHS—SS-biotin from Pierce Chemical (Rockford, Ill.).

If necessary, the cDNA molecules of the first and second cDNA populations are modified so that the molecules are not affected by the conditions or reagents which are used to cleave or release the selectable tags. Preferably, the cDNA molecules are modified prior to attachment of the selectable tags. For example, the cDNA molecules can be methylated by DNA methylase enzymes (e.g., CpG methylase) using standard techniques, prior to attachment of selectable tags comprising polynucleotide sequences. Methylation of cDNA protects the cDNA molecules from digestion by restriction enzymes which are subsequently used to cleave the selectable tags.

In one embodiment, the selectable tag comprises an polynucleotide with an attached biotin molecule and a double-stranded region containing the sequence of a rare restriction endonuclease cut site. In another embodiment, the selectable tag comprises an oligonucleotide with a single-stranded overhang and a double-stranded region containing a rare restriction enzyme cut site.

As used herein, a "rare restriction endonuclease cut site" comprises at least a five base-pair target sequence, and preferably comprises a six base-pair target sequence, for a restriction endonuclease. Examples of restriction endonucleases which cut a 5-base pair target sequence include Bbv I; Bce I; Eco RII; Fau I; and Hga I. Examples of restriction endonucleases which cut a 6-base pair target sequence include Ava I; Bam HI; Bgl II; Eco RI; Hind III; Hpa I; Kpn I; Pst I, Sma I; Sst I; Sal I; and Xma I. Other restriction endonucleases which target a rare restriction endonuclease cut site can be readily identified by those skilled in the art.

In one embodiment, a first selectable tag for attachment to cDNA molecules of a first cDNA population comprises a 6-base pair double-stranded oligonucleotide defining a Sma I target site, which has a biotin molecule attached to the 5'-end of one of the oligonucleotide strands. This tag is represented schematically below:

```
        Biotin-5'CCCGGG 3'
                GGGCCC
                -Sma I-
```

In this embodiment, a second selectable tag for attachment to the cDNA molecules of a second cDNA population comprises an oligonucleotide that has a 6-base pair double-stranded region defining a Sal I target site, and a 15 base single-stranded 5' overhang. This tag is represented schematically below:

```
    5'GTCATGCATAGCAATTGTCGAC 3'    (SEQ ID NO: 1)
                     ACAGCTG
                     -Sal I-
```

In a preferred embodiment, a first selectable tag for attachment to cDNA molecules of a first population comprises an oligonucleotide that has a six base pair double-stranded region and an 11 base 5' single-stranded overhang. A biotin molecule is attached to the 5' end of the longer oligonucleotide strand. The shorter oligonucleotide strand is phosphorylated at the 5' end to allow for blunt-end ligation of the selectable tag to the molecules of the target cDNA population. The 11 base 5' overhang comprises a six base nucleotide sequence which, when annealed with a single-stranded oligonucleotide comprising the complementary sequence, forms a Sma I restriction site. This selectable tag, hereinafter called "Tag 1," is represented schematically below. In this schematic representation, the sequence that forms the Sma I site is underlined, and the 5'-phosphate on the shorter oligonucleotide strand is shown by a "P".

```
Biotin-5'TCCCCCGGGGGAATCG 3'         (SEQ ID NO: 2)
              Sma I    3'CTTAGC-P 5'
```

In this embodiment, a second selectable tag for attachment to the cDNA molecules of a second cDNA population comprises and oligonucleotide that has a six base pair double-stranded region and a 21 base 5' single-stranded overhang. The shorter oligonucleotide strand is phosphorylated at the 5' end to allow for blunt-end ligation of the selectable tag to molecules of the target cDNA population. The 21 base 5' overhang comprises a nucleotide sequence which, when annealed with a single-stranded oligonucleotide comprising the complementary sequence, forms a Pml I restriction site. This selectable tag, hereinafter called "Tag 2," is represented schematically below. In this schematic representation, the sequence that forms the Pml I site is underlined, and the 5'-phosphate on the shorter oligonucleotide strand is shown by a "P".

```
5'ATGCATAGCAACCTCACGTGTGAATCG 3'     (SEQ ID NO: 3)
                   Pml I 3'CTTAGC-P 5'
```

Each of the tags described above can be attached to the cDNA molecules of the respective cDNA populations with standard blunt-end ligation techniques, for example as described in Sambrook et al., 1989, supra. Prior to attachment of the first and second selectable tags to the molecules of the respective cDNA populations, the cDNA molecules are preferably methylated by a DNA methylase as described above.

Once selectable tags have been attached to the cDNA molecules, some or all of the molecules from the first and second cDNA population are denatured and annealed with each other. Annealing of cDNA molecules from one cDNA population with cDNA molecules from another population is also referred to herein as "cross-hybridization."

As used herein, to "denature" a double-stranded nucleic acid means to disrupting the hydrogen bonds between the purine and pyrimidine bases of both nucleic acid strands, so that the strands are separated. Denaturation of double-stranded nucleic acids can be achieved by heating or by exposing the nucleic acids to a low salt concentration. One skilled in the art can readily choose conditions under which the present double-stranded cDNA denatures. For purposes of the present invention, it is generally sufficient to heat aqueous solutions comprising cDNA to approximately 100° C. for at least one minute in water, TE buffer (10 mM Tris-HCl; 1 mM EDTA, pH 7.6), or the subtractive hybridization solution (50 mM HEPES, pH 7.6; 2 mM EDTA; 500 mM NaCl; 0.2% SDS) of Sive et al., Nucl. Acids. Res. 16: 10937, 1988. Because single-stranded cDNA can also form internal hydrogen bonds between complementary bases within the molecule, single-stranded cDNA molecules are preferably also denatured prior to cross-hybridization. In the practice of the present invention, the cDNA molecules of the first and second cDNA populations can be denatured separately and then mixed together, or can be mixed prior to denaturation.

After denaturing, cDNA molecules from the first and second populations are annealed or "cross-hybridized," so that cDNA molecules with sufficient complementarity form duplex DNA molecules. Annealing occurs upon removal of the conditions which caused denaturation; for example, by cooling or adding an appropriate amount of a salt to an aqueous solution comprising denatured cDNA molecules. As used herein, the "annealing" of denatured nucleic acids refers to the formation of hydrogen bonds between a sufficient number of purine and pyrimidine bases of two complementary nucleic acid strands, so that the two strands form a nucleic acid molecule with at least one double-stranded region.

Cross-hybridization of cDNA molecules from the first and second cDNA populations can be carried out in solid or liquid phase, as is within the skill in the art. Preferably, cross-hybridization is carried out in the liquid phase. Liquid phase cross-hybridization is conveniently performed in any appropriate container, such as 0.5-1.5 ml plastic microcentrifuge tubes or microtiter plates. Generally, cross-hybridization is carried out in volumes ranging from 0.1 to 1000 microliters, for example from 1 to 50 microliters. The particular container as well as the final volumes used for cross-hybridization can be easily adapted by those skilled in the art to obtain the desired result.

One skilled in the art can readily determine the appropriate amount of cDNA from each cDNA population to be used in performing the cross-hybridization. In general, amounts of cDNA from each population in the range of 0.1 to 100 micrograms can be used. Typically, the cross-hybridization is performed with an excess of cDNA from one cDNA population relative to the other. For example, a 1000-fold excess, preferably a 500-fold excess, more preferably a 100-fold excess, and particularly preferably a 20-fold excess of cDNA from one cDNA population relative to the other can be used for cross-hybridization. In one embodiment, four micrograms of cDNA from a first cDNA population is hybridized to 200 nanograms of cDNA from a second cDNA population.

Preferably, an excess amount of cDNA from the biological sample which represents a standard or normal condition is cross-hybridized with the cDNA from a biological sample which represents a test or diseased condition. For example, if the first and second biological samples are derived from normal and tumor tissue, respectively, then an excess of cDNA from the normal sample is hybridized to cDNA from the tumor sample. Under such conditions essentially all the tumor cDNA anneals to complementary molecules from the normal cDNA population. Any sequence mismatches between hybridized cDNA are thus due to the presence of regions in the molecules from the tumor sample cDNA population which are different from the corresponding normal cDNA molecules. As is described in more detail below, the mismatched regions in the cross-hybridized double-stranded cDNA represent alternatively spliced regions in the original RNA molecule from which the cDNA was synthesized.

The cross-hybridization of cDNA molecules from a first and second cDNA population creates a mixed population of tagged cDNA molecules. This mixed population comprises three subpopulations: 1) single-stranded cDNA molecules from both populations; 2) double-stranded cDNA comprising cDNA molecules from only the first or only the second cDNA populations; and 3) double-stranded cDNA comprising one cDNA molecule from the first cDNA population and one cDNA molecule from the second cDNA population.

It is apparent that the cDNA molecules from only the first or only the second subpopulations described above comprise only one type of selectable tag. However, double-stranded cDNA from the third subpopulation comprises both selectable tag types. In the practice of the present method, double-stranded cDNA from the third subpopulation are isolated by selecting for one selectable tag to obtain a first selected population. The molecules of the first selected population are then subjected to a second isolation step, in which those molecules which also contain the other selectable tag are selected.

This isolation process is illustrated below and in FIGS. 3A-3C with respect to a preferred embodiment of the invention, in which two RNA populations from different physiologic states are used. However, it is understood that the present method is not restricted to isolating alternative splice forms from RNA representing different physiological states, nor is the present method restricted to the particular selectable tags, affinity media or linking moieties described below.

Figure 2A:
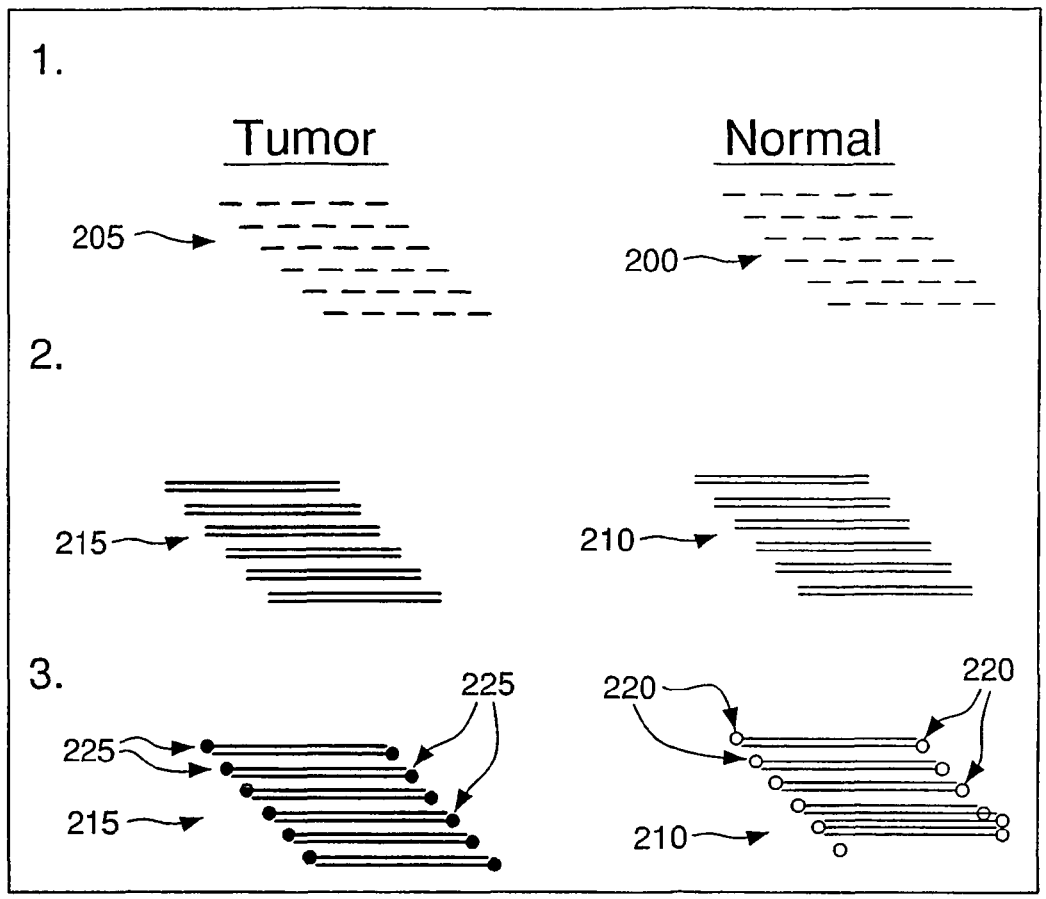
FIGS. 2A-2E are diagrams showing the isolation and identification of alternatively spliced RNA according to one embodiment of the invention.

In step 1 of FIG. 2A, a first RNA population 200 is obtained from normal tissue, and a second RNA population 205 is obtained from tumor tissue. In step 2, molecules of the first and second RNA populations are then converted into first and second double-stranded cDNA populations 210 and 215, respectively, as described above. Double-stranded cDNA populations 210 and 215 are blunt-ended with Eco RV and methylated with CpG methylase.

First cDNA population 210 is tagged with a first selectable tag 220 in step 3. First selectable tag 220 preferably comprises Tag 1 described above. Also in step 3, molecules of the second cDNA population 215 are tagged with a second selectable tag 225. The second selectable tag 225 preferably comprises Tag 2 described above.

Figure 2B:
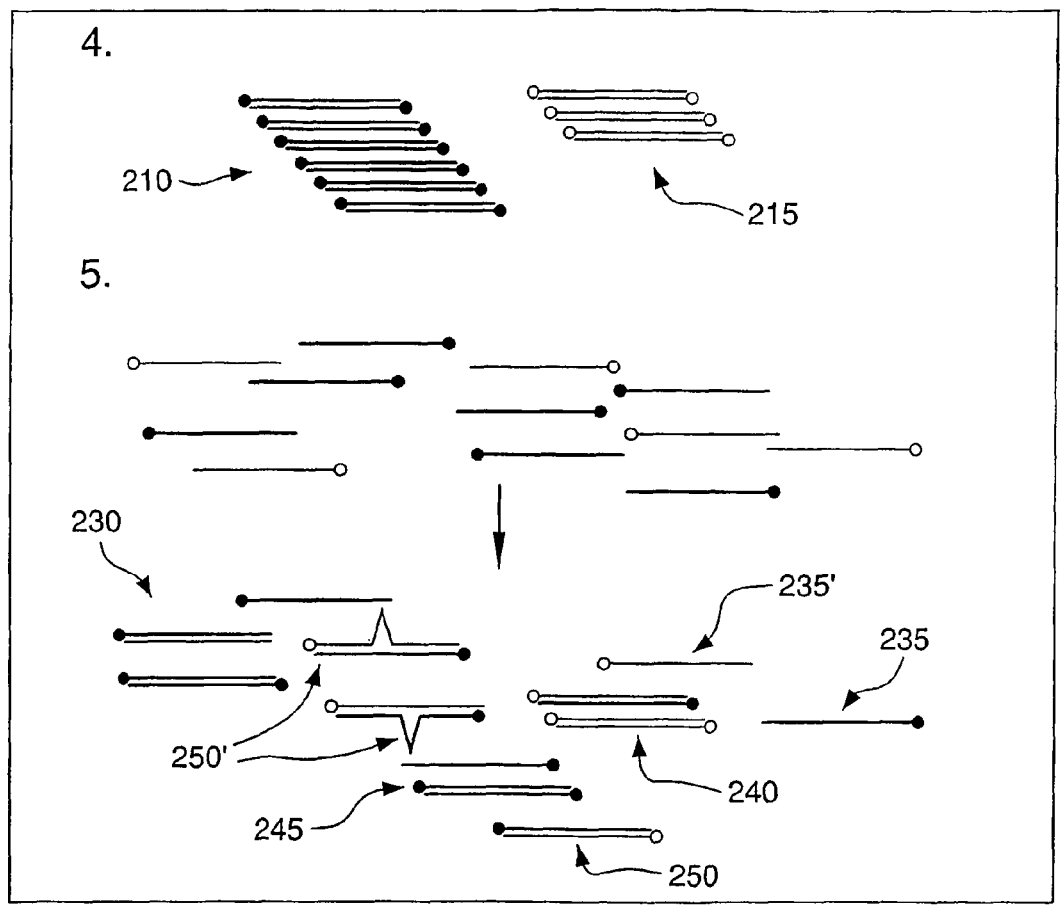

An excess of double-stranded cDNA molecules from first cDNA population 210 is mixed with cDNA molecules from second cDNA population 215 in step 4 of FIG. 2B. The mixed cDNA molecules are then denatured and annealed in step 5 to form a mixed population 230. Mixed population 230 comprises single-stranded cDNA molecules 235 and 235' from the first and second cDNA populations, respectively; double-stranded cDNA 240 wherein both strands are from the first cDNA population; double-stranded cDNA 245 wherein both strands are from the second cDNA population; and double-stranded cDNA 250 and 250' comprising one strand from the first cDNA population and one strand from the second cDNA population. The two strands in double-stranded cDNA 250 are perfectly matched, and the two strands in double-stranded cDNA 250' comprise mismatched sequences representing an alternatively spliced region.

Figure 2C:
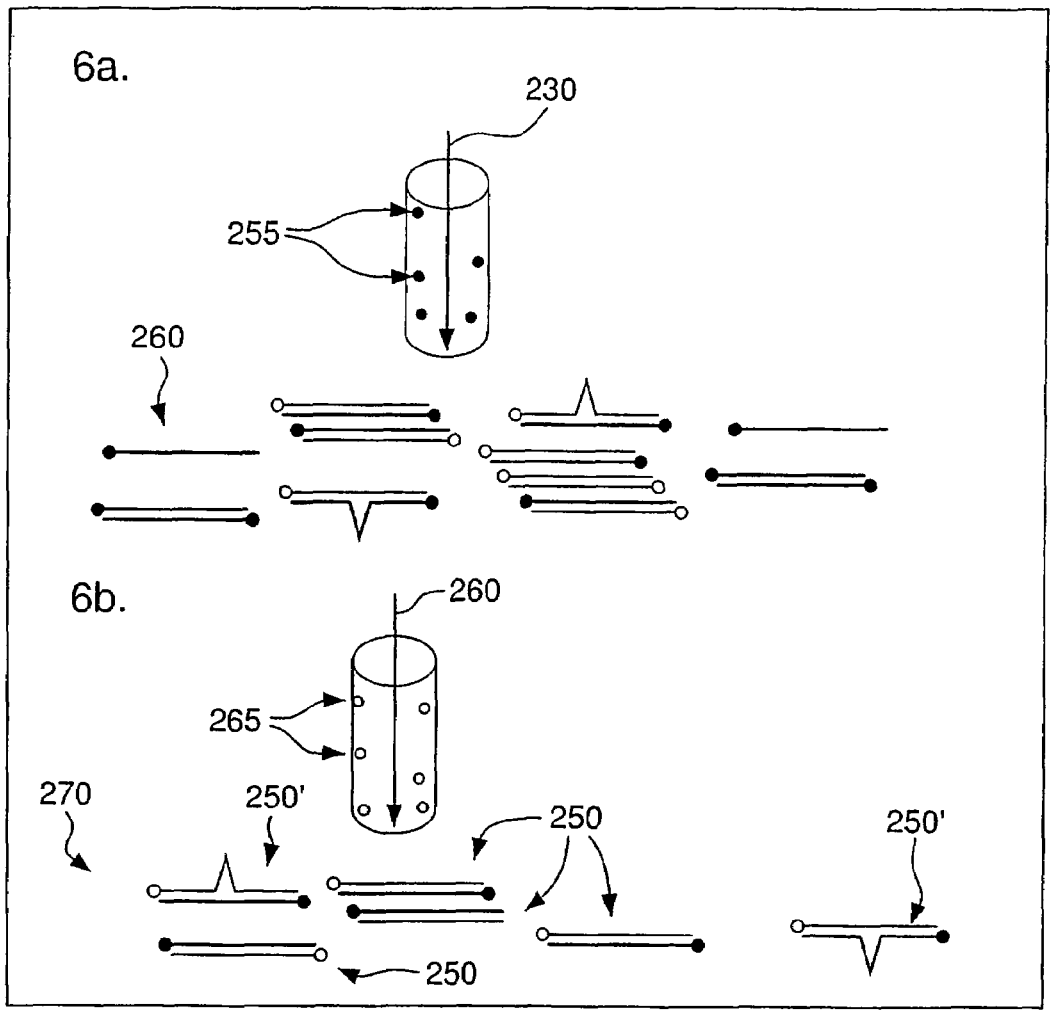

In step 6a of FIG. 2C, the mixed population 230 is contacted with an affinity medium 255 comprising avidin, which selectively binds the biotin molecules of the first selectable tag 220. The affinity medium 255 thus retains the following molecules from the mixed population: single-stranded cDNA molecules 235 from the first cDNA population; double-stranded cDNA 240 in which both cDNA molecules are derived from the first cDNA population; and double-stranded cDNA 250 and 250' in which one cDNA molecule is derived from the first cDNA population and the other cDNA molecule is derived from the second cDNA population. Single-stranded cDNA molecules 235' from the second cDNA population and double-stranded cDNA 245 in which both strands are derived from the second cDNA population are not retained. The column material is then incubated with an oligonucleotide that hybridizes with the 11 base pair overhang of SEQ ID NO: 1 to form a Sma I restrictions site. This oligonucleotide is shown below:

```
                5' CGATTC
```

The column is then washed to remove any unbound oligonucleotide. The molecules retained by the affinity medium 255 are released by digestion of the first selectable tag 220 with Sma I, to form a first selected population 260. The previous methylation of the cDNA molecules from the first cDNA population 210 and second cDNA population 215 prevents cleavage of the cDNA molecules at any internal Sma I site.

In step 6b of FIG. 2C, the first selected population 260 is contacted with an affinity medium 265 comprising a polynucleotide complementary to the 21-base pair 5' overhang of the second selectable tag 225. The sequence of the polynucleotide comprising affinity medium 265 is shown below:

```
    ACACGTGAGGTTGCTATGCAT        (SEQ ID NO: 4)
```

Hybridization of affinity medium 265 to the 21 base pair 5' overhang of the second selectable tag 225 creates a Pml I restriction site. The affinity medium 265 thus retains double-stranded cDNA 250 and 250', in which one cDNA molecule is derived from the first cDNA population and the other cDNA molecule is derived from the second cDNA population. Single-stranded cDNA molecules 235 from the first cDNA population and double-stranded cDNA 240 in which both cDNA molecules are derived from the first cDNA population are not retained.

The double-stranded cDNA 250 and 250' are then separated from the affinity medium 265 by digestion of the second selectable tag 225 with Pml I to produce a second selected population 270. The previous methylation of the cDNA molecules from the first cDNA population 200 and second cDNA population 210 prevents cleavage of the cDNA molecules at any internal Pml I site.

It is understood that order in which the mixed population 230 is contacted with the affinity media 255 and 265 is not critical. Thus, double-stranded cDNA 250 and 250' can also be isolated by first contacting the mixed population 230 with affinity medium 265 to obtain a first selected population comprising single-stranded cDNA molecules 235' from the second cDNA population and double-stranded cDNA 250 and 250'. The first selected population can then be contacted with affinity medium 255 to select for double-stranded cDNA 250 and 250'.

As stated above, affinity media 255 and 265 are exemplary. In the practice of the present method, the affinity media can comprise any moiety which selectively binds to one of the selectable tags attached to the cDNA molecules.

In one embodiment, the affinity media comprises a solid carrier comprising the other compound of an affinity pair as described above. Suitable solid carriers can comprise, for example, cellulose and cellulose derivatives; polyacrylamide; polystyrenes; polysaccharides such as dextran or agarose; rubber; glass; nylon; polyacrylate; polyvinyltoluene; styrenebutadiamine copolymers; polyacrolein; polyurethane; poly(methyl methacrylate); and combinations thereof. In preferred embodiments, the material comprising the affinity media comprises a multiplicity of functionalities; e.g., amino, carboxy, imino, or the like, to which one member of an affinity pair can be bonded.

Materials comprising affinity media can comprise free particles. Affinity media comprising particles are conveniently in the form of beads or microspheres, and preferably have an average diameter of from about 0.2 to about 20 microns. Such particles or microspheres can be readily prepared by standard techniques, or are commercially available. Alternatively, the affinity media can be affixed to an apparatus such as an affinity chromatography column, filter, or a plastic or glass surface (e.g., microtiter plates, dipstick systems or test tubes). A preferred apparatus for performing separations with the affinity media is an affinity chromatography column.

Moieties capable of selectively binding to selectable tags can be readily attached to affinity media. For example, biotin derivatives can be prepared with functionalities which are reactive towards amines, phenols, imidazoles, aldehydes, carboxylic acids and thiols. Haptens and other biological molecules can be coupled to agarose and polyacrylamides as described, for example, Cuatrecasas, *J Biol. Chem.* 245, 3059-3065, 1970 and Jacoby W B et al., *Meth. Enzymol.*, Volume 34, Academic Press, New York, 1974.

The affinity media can comprise materials other than a solid carrier. For example, affinity media can comprise a substance whose chemical or physical characteristics allow separation of bound material by electric or magnetic fields, phase extraction, or precipitation. In a preferred embodiment, such affinity media comprise magnetic particles.

Moieties capable of binding to selectable tags can be readily attached to magnetic particles, for example as disclosed in U.S. Pat. No. 5,512,439, the entire disclosure of which is herein incorporated by reference. Magnetic particles can also be derivatized by providing a surface coating of a polymer carrying functional groups such as: polyurethane together with a polyglycol to provide hydroxyl groups; a cellulose derivative to provide hydroxyl groups; a polymer or copolymer of acrylic acid or methacrylic acid to provide carboxyl groups; or an aminoalkylated polymer to provide amino groups, as described in U.S. Pat. No. 4,654,267, the entire disclosure of which is herein incorporated by reference. Moieties which bind to selectable tags are then attached to these functional groups.

In a preferred embodiment, affinity media comprising magnetic particles are prepared by attaching avidin or streptavidin attached to the particles; e.g., via a hydroxyl group. In a particularly preferred embodiment, affinity media comprising magnetic particles are prepared; e.g., by linking a nucleic acid to the particles by forming a phosphoramidate linkage between the nucleic acid and an amino group on the particle.

As described above, EDNA comprising a selectable tag is contacted with an affinity medium comprising the appropriate binding partner, under conditions suitable for effecting binding between the selectable tag and the affinity medium. One skilled in the art can readily determine the conditions under which this binding can be effected. For example, if the selectable tag and affinity medium each comprise a polynucleotide, conditions similar to those described above for cross-hybridization of cDNA molecules should also allow hybridization between the tag and affinity medium.

The cDNA molecules which are bound to the affinity medium by a selectable tag are separated from unbound material by methods appropriate to the particular type of affinity medium used. For example, if the affinity medium comprises free particles, separation of bound material can be accomplished by centrifugation or filtration of the particles from the general solution. If the affinity medium comprises an affinity chromatography column, the bound material can be conveniently separated by washing the unbound material from the column with a suitable buffer.

Recovery of the bound material from affinity media is accomplished by subjecting the affinity media to conditions suitable for cleaving or separating the selectable tag (or a portion thereof) from the cDNA molecule. Alternatively, the affinity medium is subjected to conditions suitable for reversing the binding of the selectable tag to the medium.

In another embodiment, the moiety attached to the affinity medium which specifically binds to the selectable tag (or a portion thereof) is cleavable or removable from the affinity medium itself. Moieties bound to the affinity media which are cleavable or removable can comprise a specific chemical or enzymatic cleavage site as described above for the selectable tags.

As discussed above, the sequential contact of a mixed cDNA population with the affinity media produces a selected population comprising double-stranded cDNA, in which each double-stranded cDNA comprises one EDNA molecule derived from the first cDNA population and one cDNA molecule derived from the second cDNA population. Of these double-stranded cDNA, some comprise cDNA molecules with perfectly matched nucleotide sequences and some comprise cDNA molecules with mismatched nucleotide sequences. The mismatched sequences represent alternatively spliced regions in one of the cDNA molecules. The other cDNA molecule of the double-stranded cDNA represents the normally spliced molecule. Thus, it is from this population of double-stranded cDNA that a plurality of molecules representing alternatively spliced RNA can be isolated, in conjunction with their normally spliced counterparts.

The mismatched sequences in these double-stranded cDNA result in at least one portion of the cDNA being single-stranded. The single-stranded portions can comprise a single-base mismatch or can comprise a mismatch between plurality of nucleotides. It is understood that the single-stranded portion or portions present in these double-stranded cDNA cannot be so large as to prevent formation of a stable DNA duplex. In the practice of the present method, double-stranded cDNA comprising cDNA molecules with mismatched sequences are isolated with reagents which bind single-stranded regions of DNA.

Suitable reagents which bind to regions of single-stranded DNA include, *E. coli* single-stranded binding protein (see Webster G et al., *FEBS Lett.* 411, 313-316, 1997); antibodies which bind to single-stranded DNA; enzymes (e.g., resolvases) which bind to single-stranded DNA, and ion exchange resins capable of binding single stranded nucleic acids, such as are described in U.S. Pat. No. 6,504,021 of Kristyanne et al., the entire disclosure of which is herein incorporated by reference. A suitable ion exchange resin capable of binding single stranded nucleic acids is the Solid Phase Oligo/Protein Elimination (SOPE™) resin available from Edge Biosystems, Gaithersburg, Md. Preferably, enzymes which bind to single-stranded DNA for use in the present methods lack any catalytic activity, or are used under conditions which do not allow catalytic activity to occur, such as are described in U.S. Pat. No. 6,110,684, the entire disclosure of which is herein incorporated by reference. One skilled in the art can readily determine the conditions under which double-stranded cDNA comprising mismatched sequences can bind to and be separated from the reagents which bind single-stranded DNA.

The reagents which bind single-stranded DNA can be incorporated into materials such as those described above which comprise the affinity media. In a preferred embodiment, double-stranded cDNA comprising mismatched sequences is isolated on an affinity column comprising a reagent which binds single-stranded DNA. Preparation of such affinity columns are within the skill in the art. Suitable affinity columns comprising a reagent which binds single-stranded DNA are also available commercially. For example, an affinity column comprising an antibody which binds single-stranded DNA is available from Biomol Research Laboratories, Inc. (Plymouth Meeting, Pa.). In a preferred embodiment, DNA is bound to SOPE™ resin for 30 min. at room temperature in $H_2O$. As shown in Example 1 below and in FIG. 3, double-stranded DNA with a base mismatch of 6-8 bases can be precipitated with the SOPE™ resin.

The double-stranded cDNA isolated by the single-stranded DNA binding reagent comprises one cDNA molecule which represents an alternatively spliced RNA. The other cDNA molecule in this double-stranded cDNA represents the normally spliced counterpart of the alternatively spliced RNA. A plurality of such mismatched double-stranded cDNA are isolated, representing different pairs of alternatively spliced and normal molecules. In the practice of the invention, the two cDNA molecules in each mismatched double-stranded cDNA duplex are coupled. As used herein, "coupled" means that the two cDNA molecules in the double-stranded cDNA are linked such that their association is preserved in subsequent analysis steps. Preferably, coupling of the cDNA molecules comprises covalent linking of the two strands by a chemical bond or a linking moiety. Suitable linking moieties can comprise polypeptides or polynucleotides.

The isolation of double-stranded cDNA comprising mismatch regions, and the coupling of strands in each double-stranded duplex so isolated is illustrated below and in FIG. 2D with respect to one preferred embodiment of the invention. However, it is understood that the present method is not restricted to the particular single-stranded DNA binding reagents or linking agents described below.

Figure 2D:
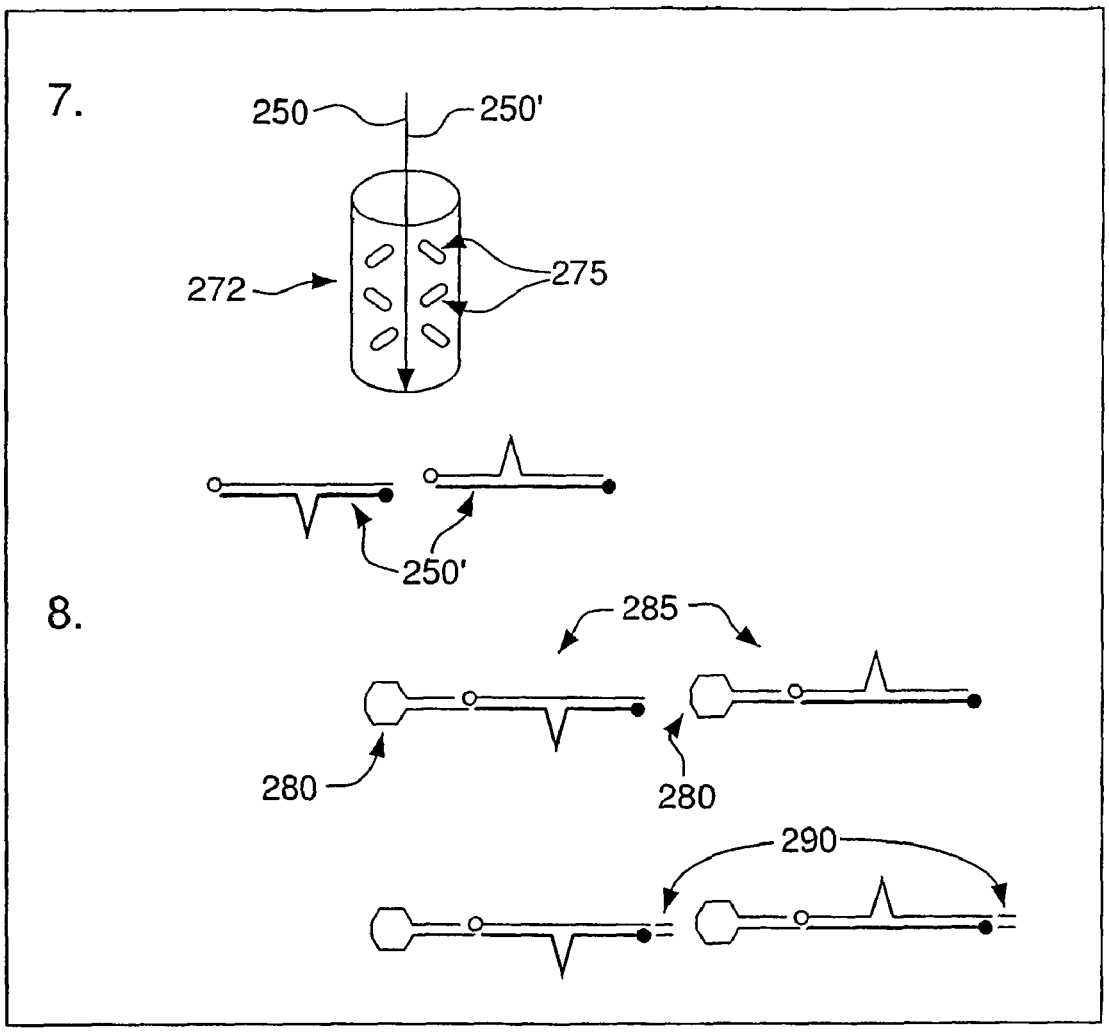

In step 7 FIG. 2D, double-stranded cDNA 250 and 250' as shown in FIG. 2C is applied to an affinity column 272 comprising a single-stranded DNA binding reagent 275. In a preferred embodiment, the single-stranded DNA binding reagent comprises SOPE™ resin obtained from Edge Biosystems (Gaithersburg, M.D.)). Double-stranded cDNA 250' (comprising mismatched sequences) is retained on the column and is separated from double-stranded cDNA 250 (which comprises perfectly matched sequences). After elution of double-stranded cDNA 250' from affinity column 272, both strands of each cDNA are coupled with linking moiety 280 in step 8 of FIG. 2D to form coupled molecules 285.

In a preferred embodiment, linking moiety 280 comprises polynucleotide "GN", which can form a DNA hairpin wherein the free ends form a complementary end with the overhang from SEQ ID NO: 3 following its annealing with its SEQ ID NO: 4 and digestion with Pml I. This polynucleotide can be ligated to the GTGT "sticky end" overhang protruding from the double-stranded cDNA which was formed by digestion of the second selectable tag 215 as described above, to covalently link the two cDNA strands. The primary nucleotide sequence of polynucleotide GN is given below:

(SEQ ID NO: 5)
5'-ACA CCG CAG ATG TCC GCA GTT ATT CCT TTT TTG GAA
TAA CTG CGG ACA TCT GCG-3'

Coupled molecules 285 comprise a plurality of molecules which represent different linked pairs of full-length alternatively spliced and normally spliced RNA molecules from the first and second biological samples. Analysis of these linked pairs can now be performed, for example to obtain information about the relative abundance of an alternatively spliced molecule, or the sequence of both normal and alternatively spliced molecules. Performance of such analyses is within the skill in the art. In one embodiment, the relative abundance of a given molecule in the final population is determined by PCR amplification of either or both strands of a coupled molecule. In a further embodiment, the sequence of both strands of a coupled molecule is determined by standard DNA sequencing techniques. For example, the coupled molecules can be sequenced directly, or PCR amplification products of either or both strands can be performed.

Figure 2E:
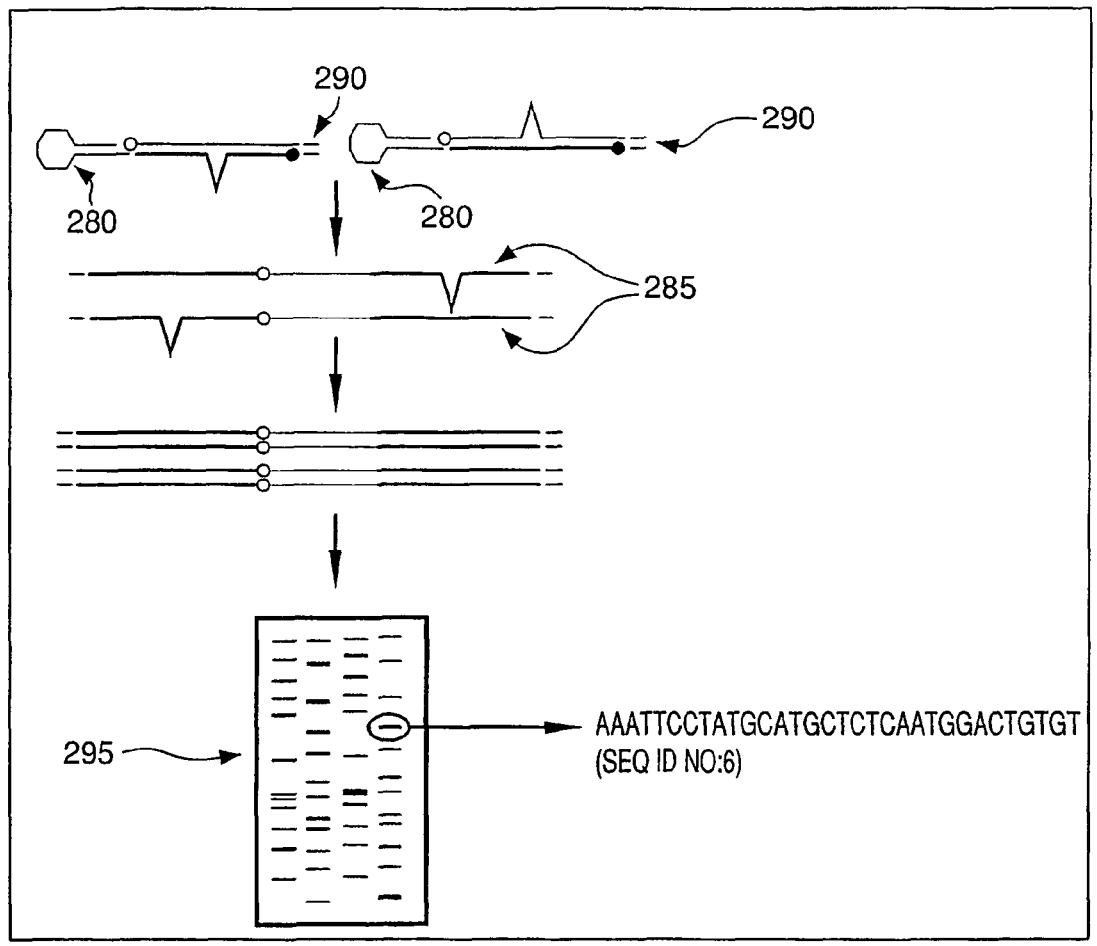

The coupled molecules can be modified to facilitate the analyses discussed above. For example, polynucleotide sequences representing targets for PCR primers can ligated to the ends of the coupled molecules. Denaturation of such molecules produces a linear polynucleotide comprising the (as yet) unknown normal and alternatively spliced sequences flanked by known sequences. This is illustrated in step 8 of FIG. 2D, which shows the blunt-end ligation of short double-stranded polynucleotide sequences 290. Polynucleotide sequences 290 comprise a target for PCR primers to the free end of coupled molecules 285. Denaturation and subsequent PCR amplification of these coupled molecules as shown in FIG. 2E produces one fragment from each coupled molecule. Each amplified fragment comprises the sequences of the normally spliced molecule and the alternatively spliced molecule from a particular coupled molecule, which flank the sequence of the linker moiety. These amplification products are then run on an agarose gel 295 under standard conditions and stained with ethidium bromide. Assuming that fluorescence of the individual fragments is proportional to length, the relative abundance of each fragment (and thus of each alternatively spliced/normal pair) will be apparent from the gel.

Individual bands can then be excised from the gel and sequenced. Preferably, the predominant species (as determined, e.g., by relative fluorescence on the gel) are excised sequenced. It is apparent that the linker moiety serves as the divider between the normal and alternatively spliced molecules. Upon sequencing, sequences of the normal and alternatively spliced molecules can be easily identified and compared; e.g., to determine what constitutes the alternative splice and to predict the reading frame.

If desired, further analysis of the normal and alternatively spliced molecules can be carried out. For example, alternatively spliced molecules can be searched against sequence databases (such as the NCBI or EMBL databases) to determine if the molecule corresponds to any known nucleotide or protein sequence. PCR primers flanking the alternatively spliced region can also be generated and used to confirm expression of the alternatively spliced RNA in tissue samples. Preferably, quantitative PCR methods are used to confirm that the alternatively spliced molecule is more expressed more abundantly in one tissue sample as compared to another.

Some or all of the components and reagents for performing the present method can be conveniently provided as a kit. For example, reagents and components for performing RNA isolation (including reverse-transcriptase and oligonucleotide primers) and reagents and components for performing cDNA synthesis (including DNA polymerase) can be provided, along with instructions for their use. A kit according to the invention can also comprise, for example, reagents and components for cross-hybridizing cDNA populations, along with instructions for their use.

A kit according to the invention can also comprise at least two different selectable tags and their corresponding affinity media, along with reagents and instructions for attaching the tags to cDNA molecules and separating the tagged cDNA molecules with the affinity media. A single-stranded DNA binding reagent for isolating double-stranded cDNA with sequence mismatches, or a linking moiety for coupling the strands of the mismatched double-stranded cDNA together, can also be provided in the present kits, along with instructions for their use.

The invention will now be illustrated by the following non-limiting example.

Example 1

Retention of Mismatched Double-Stranded DNA by SOPE™ Resin

Figure 3:
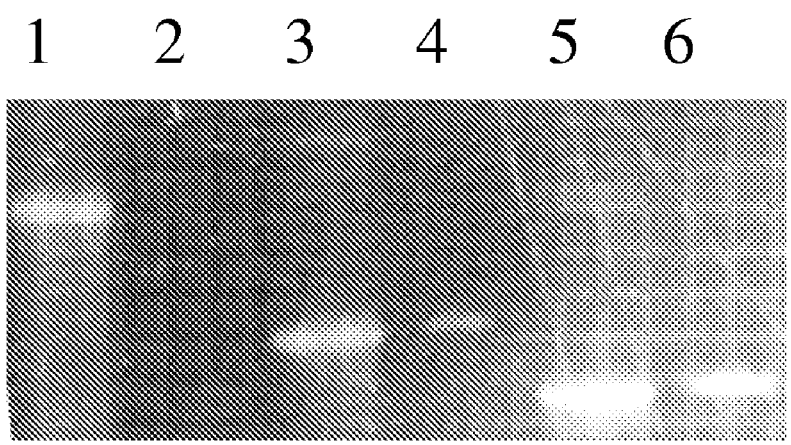
FIG. 3 is an agarose gel showing double stranded DNA with 20, 8 and 6 base mismatches either alone (lanes 1, 3 and 5, respectively) or after incubation with SOPE™ resin and removal of the resin by centrifugation (lanes 2, 4 and 6, respectively).

Oligonucleotide molecules were synthesized that were otherwise complementary except for a 4, 8, or 20 base insertion relative to one strand. After annealing, the double stranded DNA containing the mismatched regions were incubated with SOPE™ resin (Edge Biosystems, Gaithersburg, Md.) in $H_2O$ at room temperature, according to the manufacturer's instructions. Lanes 1, 3, and 5 of FIG. 3 show annealed DNA containing 20, 8 and 4 base mismatch regions, respectively, prior to binding to SOPE™ resin. SOPE™ resin was then added to the DNA. The DNA remaining in the supernatant after pelleting of the SOPE™ resin with bound DNA by centrifugation is shown in FIG. 3 (lane 2; 20 base mismatch, lane 4; 8 base mismatch, lane 6; 6 base mismatch). As can be seen from the figure, all of the double stranded DNA with a 20 base mismatch and approximately 90% of the double-stranded DNA with an 8 base mismatch was bound to the SOPE™ resin. The SOPE™ resin also appeared to bind a significant portion of the double stranded DNA with a 6 base mismatch.

All documents referred to herein are incorporated by reference in their entirety. While the present invention has been described in connection with the preferred embodiments and the various figures, it is to be understood that other similar embodiments may be used or modifications and additions made to the described embodiments for performing the same function of the present invention without deviating therefrom. Therefore, the present invention should not be limited to any single embodiment, but rather should be construed in breadth and scope in accordance with the recitation of the appended claims.

I claim:

1. A method of identifying an alternatively spliced RNA molecule in conjunction with a normally spliced counterpart RNA molecule, comprising the steps of:
  (a) obtaining a first population of cDNA molecules from a biological sample representing a first physiological condition and a second population of cDNA molecules from a biological sample representing a second physiological condition;
  (b) attaching a first selectable tag to cDNA molecules of the first cDNA population and a second selectable tag to cDNA molecules of the second cDNA population, wherein the first and second selectable tags are different;
  (c) combining, denaturing and annealing cDNA molecules from both the first and second cDNA populations, to obtain a mixed population of cDNA molecules including cross-hybridized double-stranded cDNA that comprises both a single strand that is from the first population of cDNA and that is attached to the first selectable tag, and a single strand that is from the second population of cDNA and that is attached to the second selectable tag;
  (d) isolating cross-hybridized double-stranded cDNA that comprises both the first and second selectable tags from the mixed population;
  (e) selecting from the cross-hybridized double-stranded cDNA isolated in step (d), cross-hybridized double-stranded cDNA which comprises at least one area of mismatched sequence present as an unhybridized single-stranded nucleic acid;
  (f) coupling at one end of the 3' end of one strand of a cross-hybridized double-stranded cDNA molecule selected in step (e) to the 5' end of the other strand of said cross-hybridized double-stranded cDNA molecule to form a loop and produce a coupled cross-hybridized double-stranded cDNA molecule that comprises at least one area of mismatched sequence, wherein when denatured said coupled cross-hybridized double-stranded cDNA molecule is a single linear single stranded nucleic acid molecule;
  (g) denaturing the coupled cross-hybridized double-stranded cDNA molecule to form a single linear single stranded nucleic acid molecule; and
  (h) analyzing the sequence of the linear single stranded nucleic acid molecule derived from the cross-hybridized double stranded cDNA to identify the sequence of an alternatively spliced RNA molecule through comparison of sequences derived from the first population of cDNA to sequences derived from the second population of cDNA.

2. The method of claim 1, wherein the first biological sample comprises normal tissue, and the second biological samples comprises diseased tissue.

3. The method of claim 1, wherein the first and second biological samples comprise tissue in different developmental states.

4. The method of claim 1, wherein the first biological sample comprises untreated tissue, and the second biological sample comprises tissue which has been treated with a therapeutic or toxic agent.

5. The method of claim 1, wherein first and second biological samples comprise tissue or cells from different species.

6. The method of claim 1, wherein the first and second biological samples are from a human.

7. The method of claim 2, wherein the second biological sample comprises tumor or neoplastic tissue.

8. The method of claim 7, wherein the tumor or neoplastic tissue is from a subject with acute promyelocytic leukemia; acute lymphoblastic leukemia; myeloblastic leukemia; uterine cancer; thyroid cancer; gastrointestinal tumors; dysplastic and neoplastic cervical epithelium; melanoma; breast cancer; prostate cancer; lung cancer; endometrial cancer; teratocarcinoma; colon cancer; brain and desmoplastic round cell tumors; epithelial neoplasias; gastric cancer; ovarian cancer or sarcomas, myomas, myxomas, ependymomas, fibromas, neurofibrosarcomas.

9. The method of claim 2, wherein the second biological sample comprises diseased tissue from a subject with infection, stress, disorders or conditions of the immune system; a metabolic disorder; a collagen disorder; a psychiatric disorder, a skin disorder, a liver disorder, a disorders of the arteries; an inherited red cell membrane disorder; thyroid hormone repression; endometrial hyperplasia; Alzheimer's disease; or alcoholism.

10. The method of claim 1, wherein the first and second cDNA populations are synthesized from RNA populations which have been enriched for polyA+RNA.

11. The method of claim 1, wherein at least one cDNA population comprises double-stranded cDNA.

12. The method of claim 1, wherein the first and second cDNA populations comprise double-stranded cDNA.

13. The method of claim 1, wherein the first and second selectable tags are selected from the group consisting of: biotin; avidin; streptavidin; antigens; haptens; antibodies; hormones; vitamins; receptors; carbohydrates; lectins; metals; chelators; polynucleotides; cofactor or prosthetic groups; apoproteins; effector molecules; one member of a hydrophobic interactive pair; enzyme cofactors; enzymes; polymeric acids; polymeric bases; dyes; protein binders; peptides; protein binders; and enzyme inhibitors, provided that the first and second selectable tags are different.

14. The method of claim 1, wherein the first selectable tag comprises a biotin.

15. The method of claim 1, wherein the second selectable tag comprises a biotin.

16. The method of claim 1, wherein the first selectable tag comprises a polynucleotide.

17. The method of claim 1, wherein the second selectable tag comprises a polynucleotide.

18. The method of claim 16, wherein the polynucleotide comprises, a restriction enzyme target site.

19. The method of claim 17, wherein the polynucleotide comprises a restriction enzyme target site.

20. The method of claim 1, wherein:
  i) the first selectable tag comprises a pair of olignucleotides having a longer strand and a shorter strand, wherein each strand has a 5' end, and wherein when annealed the pair of olignucleotides form a six base pair double-stranded region and an 11 base 5' single-stranded overhang, and wherein a biotin molecule is attached to the 5' end of the longer oligonucleotide strand and the 5' end of shorter oligonucleotide strand is phosphorylated at the 5' end, and wherein the 11 base 5' overhang comprises a six base nucleotide sequence which, when annealed with a single-stranded oligonucleotide comprising the complementary sequence, forms a Sma I restriction site; and
  ii) the second selectable tag comprises a pair of olignucleotides having a longer strand and a shorter strand, wherein each strand has a 5' end, and wherein when the pair of olignucleotides annealed form a six base pair double-stranded region and an 21 base 5' single-stranded overhang, and wherein the 5' end of shorter oligonucleotide strand is phosphorylated at the 5' end, and wherein the 21 base 5' overhang comprises a six base nucleotide sequence which, when annealed with a single-stranded oligonucleotide comprising a complementary sequence, forms a Pml I restriction site.

21. The method of claim 1, wherein in step (c) the cDNA molecules in the first and second cDNA populations are denatured separately, mixed, and annealed to obtain the mixed population of cDNA molecules.

22. The method of claim 1, wherein in step (c) the cDNA molecules in the first and second cDNA populations are mixed together, denatured, and annealed to obtain the mixed population of cDNA molecules.

23. The method of claim 1, wherein an excess of cDNA from one cDNA population relative to the other is used to obtain the mixed population of cDNA molecules.

24. The method of claim 2, wherein an excess of cDNA molecules from the first cDNA population relative to cDNA molecules from the second cDNA population is used to obtain the mixed population of cDNA molecules.

25. The method of claim 24, wherein a 20-fold excess of cDNA from the first cDNA population relative to cDNA molecules from the second cDNA population is used to obtain the mixed population of cDNA molecules.

26. The method of claim 1, wherein step (d) comprises:
(i) selecting molecules comprising the first selectable tag from the mixed population to obtain a first selected population; and
(ii) selecting molecules comprising the second selectable tag from the first selected population to obtain a second selected population,
wherein the second selected population comprises the mixed population double-stranded cDNA comprising a cDNA molecule from the first cDNA population and a cDNA molecule from the second cDNA population.

27. The method of claim 1, wherein step (d) comprises:
(i) selecting molecules comprising the second selectable tag from the mixed population to obtain a first selected population; and
(ii) selecting molecules comprising the first selectable tag from the first selected population to obtain a second selected population, wherein the second selected population comprises double-stranded cDNA comprising the first and second selectable tags, and also comprises a cDNA molecule from the first cDNA population and a cDNA molecule from the second cDNA population.

28. The method of claim 1, wherein step (d) comprises contacting the mixed population with an affinity medium.

29. The method of claim 28, wherein the affinity medium comprises a compound selected from the group consisting of: biotin; avidin; streptavidin; antigens; haptens; antibodies; hormones; vitamins; receptors; carbohydrates; lectins; metals; chelators; polynucleotides; cofactor or prosthetic groups; apoproteins; effector molecules; one member of a hydrophobic interactive pair; enzyme cofactors; enzymes; polymeric acids; polymeric bases; dyes; protein binders; peptides; protein binders; and enzyme inhibitors.

30. The method of claim 28, wherein the affinity medium comprises an affinity column.

31. The method of claim 28, wherein the affinity media comprises a solid carrier.

32. The method of claim 31, wherein the solid carrier is selected from the group consisting of: cellulose and cellulose derivatives; polyacrylamide; polystyrenes; polysaccharides; rubber; glass; nylon; polyacrylate; polyvinyltoluene; styrenebutadiamine copolymers; polyacrolein; polyurethane; poly(methyl methacrylate); and combinations thereof.

33. The method of claim 28, wherein the affinity medium comprises a magnetic particle.

34. The method of claim 1, wherein step (e) comprises contacting the double-stranded cDNA from step (d) with a reagent which binds sequences of single-stranded DNA.

35. The method of claim 34, wherein the reagent which binds to regions of single-stranded DNA is selected from the group consisting of a resin which binds single stranded DNA, *E. coli* single-stranded binding protein; antibodies which bind to single-stranded DNA; and enzymes which bind to single-stranded DNA.

36. The method of claim 34, wherein the reagent which binds regions of single-stranded DNA is contained in an affinity column.

37. The method of claim 1, wherein step (c) comprises covalently linking both strands of each double-stranded cDNA from step (e) to each other to obtain a coupled molecule.

38. The method of claim 37, wherein both strands of each double-stranded cDNA from step (e) are covalently linked to each other with a polynucleotide linking moiety.

39. The method of claim 38, wherein the polynucleotide linking moiety comprises SEQ ID NO: 5.

40. The method of claim 1, wherein step (h) comprises determining at least a partial nucleotide sequence for each strand of the coupled molecule.

* * * * *

UNITED STATES PATENT AND TRADEMARK OFFICE
CERTIFICATE OF CORRECTION

PATENT NO. : 7,919,238 B2  
APPLICATION NO. : 10/567808  
DATED : April 5, 2011  
INVENTOR(S) : Albert J. Wong Page 1 of 1

It is certified that error appears in the above-identified patent and that said Letters Patent is hereby corrected as shown below:

Please replace claim 37 as follows (col. 24, claim 37, line 34):

--37. The method of claim 1, wherein step (f) comprises covalently linking both strands of each double-stranded cDNA from step (e) to each other to obtain a coupled molecule.--

Signed and Sealed this
Twenty-seventh Day of September, 2011

David J. Kappos
*Director of the United States Patent and Trademark Office*